US00PP34449P2

(12) United States Plant Patent
Kleinwee

(10) Patent No.: US PP34,449 P2
(45) Date of Patent: Jul. 26, 2022

(54) ***PETUNIA* PLANT NAMED 'PEHY0060'**

(50) Latin Name: *Petunia hybrida*
Varietal Denomination: 'PEHY0060'

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/548,642

(22) Filed: Dec. 13, 2021

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824
See application file for complete search history.

(56) References Cited

PUBLICATIONS

CPVO hit on UPOV QZ PBR 2021/1876, *Petunia* plant named, 'PEHY0060', filed Jul. 16, 2021.*

* cited by examiner

*Primary Examiner* — Anne Marie Grunberg
(74) *Attorney, Agent, or Firm* — Dale Skalla

(57) ABSTRACT

A new *Petunia* plant named 'PEHY0060' particularly distinguished by its small to medium sized, yellow with pink margin flowers, medium early flowering and mounding plant habit.

1 Drawing Sheet

Latin name of the genus and species of the plant claimed: *Petunia hybrida.*

Varietal denomination: 'PEHY0060'.

BACKGROUND OF THE NEW PLANT

The present invention comprises a new *Petunia*, botanically known as *Petunia hybrida*, and hereinafter referred to by the variety name 'PEHY0060'.

'PEHY0060' is a product of a planned breeding program. The new cultivar has small to medium sized, yellow with pink margin flowers, medium early flowering and a mounding plant habit.

'PEHY0060' originated from a hybridization made in October 2017 in a controlled breeding environment in Enkhuizen, The Netherlands. The female parent was the proprietary selection 'BB1301-1V' (not patented in US). Compared to 'PEHY0060', it has a bit more trailing plant habit, has a pink color with only a small yellow coloured center of the flower, is later flowering and has a bit smaller flower.

The male parent of 'PEHY0060' was the unpatented proprietary selection 'PETBC0636-2V'; a plant with somewhat bigger flowers, later flowering, a bit more trailing plant habit, and a yellow flower color with burgundy spots.

The resulting seeds were sown in January 2018. 'PEHY0060' was selected as one flowering plant within the progeny of the stated cross in May 2018 in a controlled environment in Enkhuizen, The Netherlands.

The first act of asexual reproduction of 'PEHY0060' was accomplished when vegetative cuttings were propagated from the initial selection in June 2018 in a controlled environment in Enkhuizen, The Netherlands.

BRIEF SUMMARY OF INVENTION

Horticultural examination of plants grown from cuttings of the plant initiated in June 2018 and continuing thereafter, has demonstrated that the combination of characteristics as herein disclosed for 'PEHY0060' are firmly fixed and are retained through successive generations of asexual reproduction.

'PEHY0060' has not been observed under all possible environmental conditions. The phenotype may vary significantly with variations in environment such as temperature, light intensity, and day length.

A Plant Breeder's Right for this cultivar was applied for in the European Union on Jul. 16, 2021, No. 2021/1876. 'PEHY0060' has not been made publicly available prior to the effective filing date of this application, notwithstanding any disclosure that may have been made less than one year prior to the effective filing date of this application by the inventor or another who obtained 'PEHY0060' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0060' with colors being as true as possible with an illustration of this type.

Figure 1:
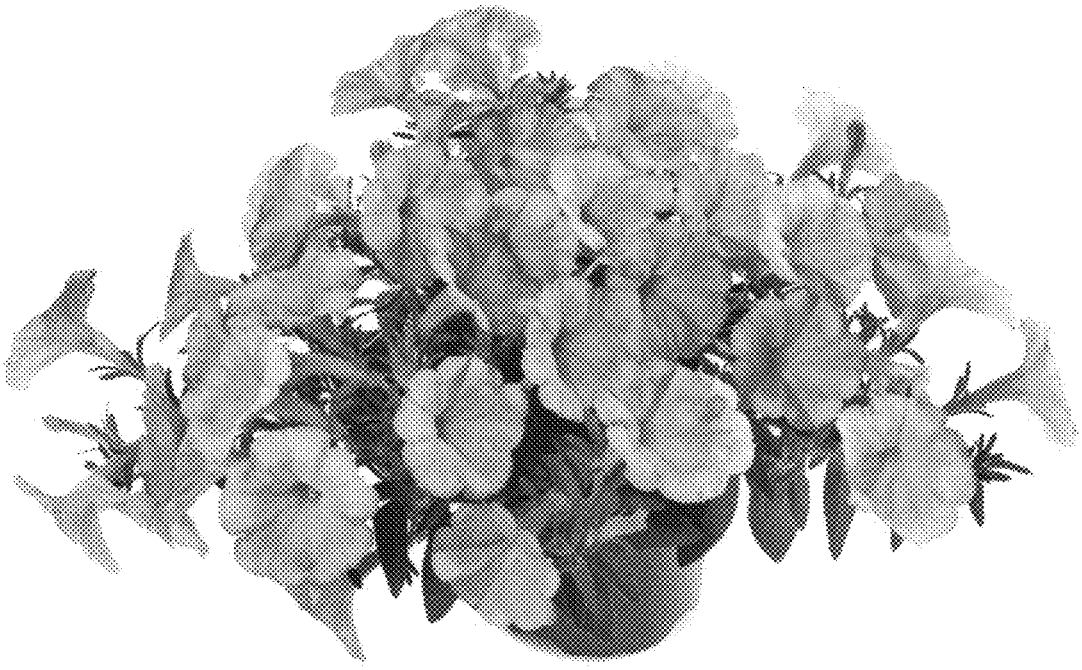
Figure 2:
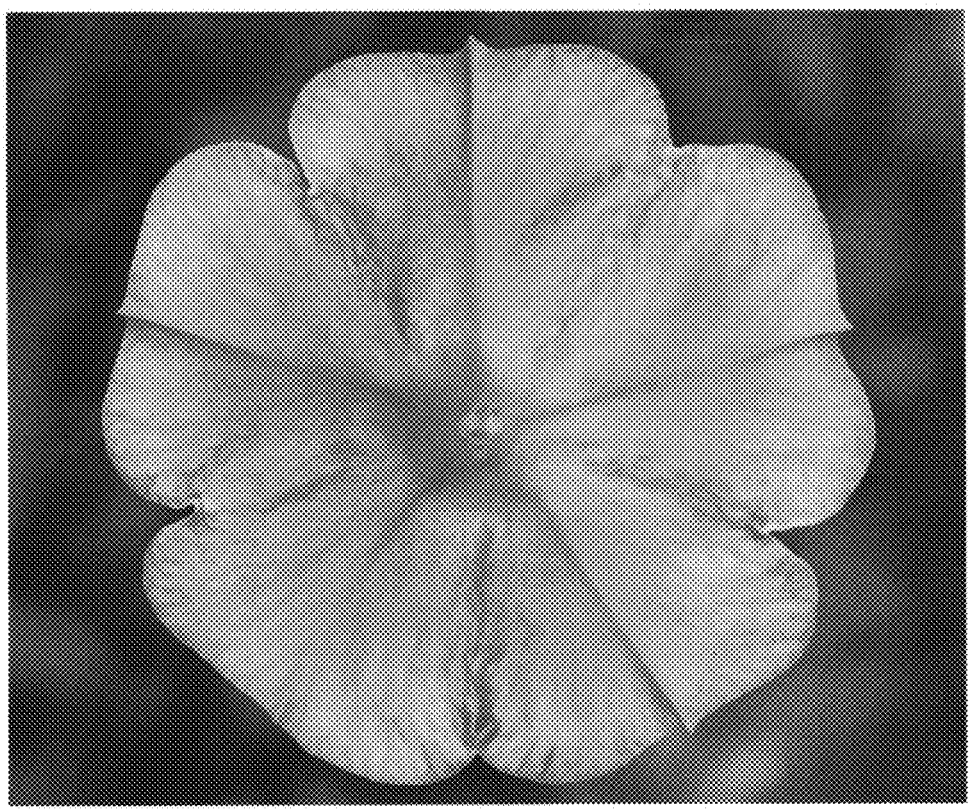

The photographic drawings show in FIG. 1 a flowering plant of the new variety and in FIG. 2 a close-up of the flowers.

DETAILED BOTANICAL DESCRIPTION

The aforementioned photographs were taken in May 2020 from plants growing indoor in 12 cm pots in Andijk, The Netherlands. These plants were approximately 12 weeks of age.

The plant descriptions and measurements were taken in September 2021 in Enkhuizen, The Netherlands on approximately 12 week old plants that were growing in containers.

Color references are made to The Royal Horticultural Society Colour Chart (R.H.S.) 2001.

TABLE 1

DIFFERENCES BETWEEN THE NEW VARIETY 'PEHY0060' AND A SIMILAR VARIETY

| | 'PEHY0060' | 'Indian summer' (not patented) |
|---|---|---|
| Plant vigor: | Medium | Strong |
| Flower color: | Relatively more pink color | Relatively more yellow color |
| Plant habit: | Mounding | Trailing |

Plant:
- *Form, growth and habit.*—Mounding plant habit.
- *Plant height.*—22 cm.
- *Plant height (inflorescence included).*—25 cm.
- *Plant diameter (width).*—Approximately 30 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 137C.
- *Immature leaf, color lower surface.*—RHS 137D.
- *Mature leaf, color upper surface.*—RHS 137A.
- *Mature leaf, color lower surface.*—RHS 137C.
- *Length.*—3.0-4.5 cm.
- *Width.*—1.5-2.0 cm.
- *Shape.*—Ovate.
- *Base shape.*—Shortly Attenuate.
- *Apex shape.*—Acute.
- *Margin.*—Entire.
- *Texture, upper surface.*—Densely covered with short hairs.
- *Lower surface.*—Densely covered with short hairs.
- *Color of veins, upper surface.*—RHS 144A.
- *Color of veins, lower surface.*—RHS 144A.
- *Petiole color.*—RHS 144A.
- *Length.*—0.4 cm.
- *Diameter.*—0.2 cm.
- *Petiole texture.*—Densely covered with short hairs.

Stem:
- *Quantity of main branches per plant.*—4-5.
- *Color of stem.*—RHS 144A.
- *Length of stem.*—20 cm.
- *Diameter.*—0.3 cm.
- *Length of internodes.*—1.5-3.5 cm.
- *Texture.*—Dense, mostly glandular short hairs.
- *Color of pedicel.*—RHS 144A.
- *Length of pedicel.*—2.0 cm.
- *Diameter of pedicel.*—0.3 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium early flowering in greenhouse, flowering throughout the summer months.
- *Quantity of inflorescences per plant.*—Approximately 45.
- *Lastingness of individual blooms on the plant.*—About 7 days.
- *Fragrance.*—Rather strong smell.

Bud (just when opening):
- *Color.*—RHS 144D, 29B towards top.
- *Length.*—3.2 cm.
- *Width.*—0.6 cm.
- *Shape.*—Oblong.

Immature inflorescence:
- *Flower horizontal diameter.*—1.6 cm.
- *Color petals, upper surface.*—RHS 14B, RHS 51C towards margin.
- *Color petals, lower surface.*—RHS 11B, RHS 29D towards margin veins 144B.

Mature flower:
- *Flower horizontal diameter.*—6 cm.
- *Flower height (vertical).*—2.5-3.5 cm.
- *Color upper surface.*—RHS 14B, RHS 50C towards margin.
- *Color lower surface.*—RHS 23D.
- *Conspicuousness of veins.*—Weak to medium.
- *Apex shape.*—Acuminate.
- *Margin.*—Entire.
- *Waviness of margin.*—Medium.
- *Petal lobation.*—Medium.
- *Petal texture, upper surface.*—Smooth.
- *Petal texture, lower surface.*—Smooth, occasionally a short hair.
- *Corolla tube color outside.*—RHS 160A.
- *Corolla tube color inside.*—RHS 163A.
- *Conspicuousness of veins in tube.*—Medium.
- *Corolla tube length.*—2.5 cm.
- *Corolla tube texture, outside.*—Rather dense and short glandular hairs.
- *Corolla tube texture, inside.*—Glabrous.

Calyx:
- *Color of sepal, upper surface.*—RHS 137A.
- *Color of sepal, lower surface.*—RHS 137B.
- *Length.*—1.9 cm.
- *Width.*—0.3 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.2 cm.
- *Style color.*—RHS 145C.

*Style length.*—1.4 cm.
*Stigma color.*—RHS 142B.
*Stamens.*—
*Quantity per flower.*—5.
*Color of filaments.*—RHS 149D.
*Length filaments.*—1.2 cm.
*Anther color.*—RHS 159D.
*Anther length.*—0.2 cm.
*Anther shape.*—Elliptical.
*Color of pollen.*—RHS 158C.
*Pollen amount.*—Medium.
*Fertility/seed set.*—Has not been observed on this hybrid.
*Disease/pest resistance.*—Has not been observed on this hybrid.

What is claimed is:

1. A new and distinct variety of *Petunia* plant named 'PEHY0060' substantially as illustrated and described herein.

* * * * *